(12) United States Patent
Gaiser et al.

(10) Patent No.: US 6,544,226 B1
(45) Date of Patent: Apr. 8, 2003

(54) OPERATIVE DEVICES THAT CAN BE REMOVABLY FITTED ON CATHETER BODIES TO TREAT TISSUE REGIONS IN THE BODY

(75) Inventors: John Gaiser, Mountain View, CA (US); David S. Utley, San Carlos, CA (US); Scott West, Livermore, CA (US)

(73) Assignee: Curon Medical, Inc., Sunnyvale, CA (US)

( * ) Notice: Subject to any disclaimer, the term of this patent is extended or adjusted under 35 U.S.C. 154(b) by 0 days.

(21) Appl. No.: 09/524,432

(22) Filed: Mar. 13, 2000

(51) Int. Cl.[7] ................................................. A61F 7/12
(52) U.S. Cl. ......................... 604/113; 604/106; 604/27
(58) Field of Search ........................ 604/113, 20, 106, 604/27, 32, 96, 124, 126, 1, 2, 101, 103, 122; 600/9, 11, 373, 372, 375; 606/27, 40, 32

(56) References Cited

U.S. PATENT DOCUMENTS

| | | | |
|---|---|---|---|
| 3,789,831 A | * | 2/1974 | Kopaniky et al. ............ 600/505 |
| 4,578,061 A | | 3/1986 | Lemelson |
| 4,785,823 A | | 11/1988 | Eggers et al. |
| 5,507,743 A | | 4/1996 | Edwards et al. |
| 5,593,406 A | * | 1/1997 | Eggers et al. ................... 606/28 |
| 5,607,422 A | * | 3/1997 | Smeets et al. .................. 606/41 |
| 5,913,865 A | | 6/1999 | Fortier et al. |
| 5,966,168 A | | 10/1999 | Miyazaki |
| 5,976,129 A | | 11/1999 | Desai |
| 6,004,316 A | * | 12/1999 | Laufer .......................... 128/898 |
| 6,071,277 A | * | 6/2000 | Farley et al. .................. 604/113 |
| 6,123,702 A | * | 9/2000 | Swanson et al. ............... 606/34 |
| 6,135,997 A | * | 10/2000 | Laufer et al. ................. 604/113 |
| 6,152,899 A | * | 11/2000 | Farley et al. .................. 604/106 |
| 6,325,798 B1 | * | 12/2001 | Edwards et al. ............... 606/41 |

\* cited by examiner

*Primary Examiner*—Joseph Pelham
*Assistant Examiner*—Vinod D Patel
(74) *Attorney, Agent, or Firm*—Ryan Kromholz & Manion

(57) ABSTRACT

A targeted tissue region in a body is treated by a tissue heating element attached to a carrier. The carrier is intended, in use, to be temporarily mounted to an exterior of a catheter body, such as an endoscope. The catheter body is deployed, with the carrier mounted on it, into the targeted tissue region. The tissue heating element is operated, e.g., to form one or more tissue lesions, after which the catheter body is retrieved from the targeted tissue region. The carrier can then be removed from the catheter body, allowing the catheter body to be subsequently used for another purpose.

63 Claims, 12 Drawing Sheets

OPERATIVE DEVICES THAT CAN BE REMOVABLY FITTED ON CATHETER BODIES TO TREAT TISSUE REGIONS IN THE BODY

FIELD OF THE INVENTION

In a general sense, the invention is directed to systems and methods for treating interior tissue regions of the body. More specifically, the invention is directed to systems and methods for treating dysfunction in body sphincters and adjoining tissue, e.g., in and around the lower esophageal sphincter and cardia of the stomach.

BACKGROUND OF THE INVENTION

As FIG. 1 shows, the esophagus 10 is a muscular tube that carries food from the mouth into the stomach 12. The muscles in the walls of the esophagus 10 contract in a wavelike manner, moving the food down to the stomach 12. The interior wall of the esophagus includes glands that secrete mucus, to aid in the movement of food by providing lubrication. The human esophagus is about twenty-five centimeters long.

The stomach 12, located in the upper left hand side of the abdomen, lays between the esophagus 10 and the small intestine 14. In people and most animals, the stomach 12 is a simple baglike organ. A human being's stomach is shaped much like a J.

The average adult stomach can hold a little over one quart (0.95 liter). The stomach 12 serves as a storage place for food. Food in the stomach 12 is discharged slowly into the intestines 14. The stomach 12 also helps digest food.

The upper end of the stomach connects with the esophagus 10 at the cardiac notch 16, at the top of the J-shape. The muscular ring called the lower esophageal sphincter 18 surrounds the opening between the esophagus 10 and the stomach 12. The funnel-shaped region of the stomach 12 immediately adjacent to the sphincter 18 is called the cardia 20. The cardia 20 comprises smooth muscle. It is not a sphincter.

The lower esophageal sphincter 18 relaxes, or opens, to allow swallowed food to enter the stomach 12. The lower esophageal sphincter 18, however, is normally closed, to keep the stomach 12 contents from flowing back into the esophagus 10.

Another sphincter, called the pyloric sphincter 22, surrounds the duodenal opening of the stomach 12. The pyloric sphincter 22 keeps non-liquid food material in the stomach 12 until it is processed into a more flowable, liquid form. The time that the stomach 12 retains food varies. Usually, the stomach 12 empties in three to five hours.

In a person suffering from gastrointestinal reflux disease (GERD), the lower esophageal sphincter 18 is subject to spontaneous relaxation. The sphincter 18 opens independent of the normal swallowing function. Acidic stomach contents surge upward into the esophagus 10, causing pain, discomfort, and damage the mucosal wall of the esophagus 10.

The stomach 12 distends to accommodate various food volumes. Over time, stomach distention can stretch the cardia 20 or otherwise cause loss of compliance in the cardia 20. Loss of compliance in the cardia 20 can also pull the lower esophageal sphincter 18 open when the stomach 12 is distended, even absent sphincter muscle relaxation. The same undesired results occur: acidic stomach contents can surge upward into the esophagus 10. Unlike the stomach, the esophagus has no natural protection against stomach acids. When the stomach contents make contact with the esophagus, heartburn or other disease symptoms, including damage to the esophagus, can occur.

Complications of GERD include esophageal erosion, esophageal ulcer, and esophageal stricture; replacement of normal esophageal epithelium with abnormal (Barrett's) epithelium; and pulmonary aspiration.

SUMMARY OF THE INVENTION

One aspect of the invention provides systems and methods for treating a targeted tissue region with a tissue heating element. The tissue heating element is incorporated in a carrier. The carrier is intended, in use, to be temporarily mounted to an exterior of an independent catheter body, such as an endoscope. The catheter body is deployed, with the carrier mounted on it, into the targeted tissue region. The tissue heating element is operated, e.g., to form one or more tissue lesions, after which the catheter body is retrieved from the targeted tissue region. The carrier can then be removed from the catheter body, allowing the catheter body to be subsequently used for another purpose.

In one embodiment, the systems and methods can be used to treat tissue regions along the gastrointestinal track, e.g., in and around the lower esophageal sphincter, to treat GERD and related dysfunctions.

Features and advantages of the inventions are set forth in the following Description and Drawings, as well as in the appended claims.

BRIEF DESCRIPTION OF THE DRAWINGS

FIG. 1 is an anatomic view of the esophagus and stomach;

FIG. 2 is a perspective view, with portions broken away, a device comprising an operative element and appended control assembly, which embodies features of the invention;

FIG. 3 is a perspective view, with portions broken away, of the device shown in FIG. 2, fitted on the distal end of a catheter body for use;

FIG. 4 is a perspective view, with portions broken away, of a device comprising an operative element and appended control assembly, snap fitted about a catheter body for use;

FIG. 5 is a diagrammatic perspective view of the device shown in FIG. 2, with the control assembly coupling the operative element to various external apparatus FIG. 6 is a perspective view of an embodiment of a device of a type shown in FIG. 2, which fits on the distal end of a catheter body, and which is intended for deployment in the esophagus to form lesions in the lower esophageal sphincter or adjoining tissue, showing the electrodes used to form the lesions in a retracted position;

FIG. 7 is a perspective view of the device shown in FIG. 6, with the top of the operative element body removed and showing the electrodes used to form the lesions in an advanced position;

FIG. 8 is an exploded proximal perspective view of the operative element associated with the device shown in FIGS. 6 and 7, showing a portion of the mechanism used to advance and retract the electrodes;

FIG. 9 is a perspective view of an embodiment of a device of a type shown in FIG. 4, which snap fits about a catheter body, and which is intended for deployment in the esophagus to form lesions in the lower esophageal sphincter or adjoining tissue, showing the electrodes used to form the lesions in a retracted position;

Figure 1:
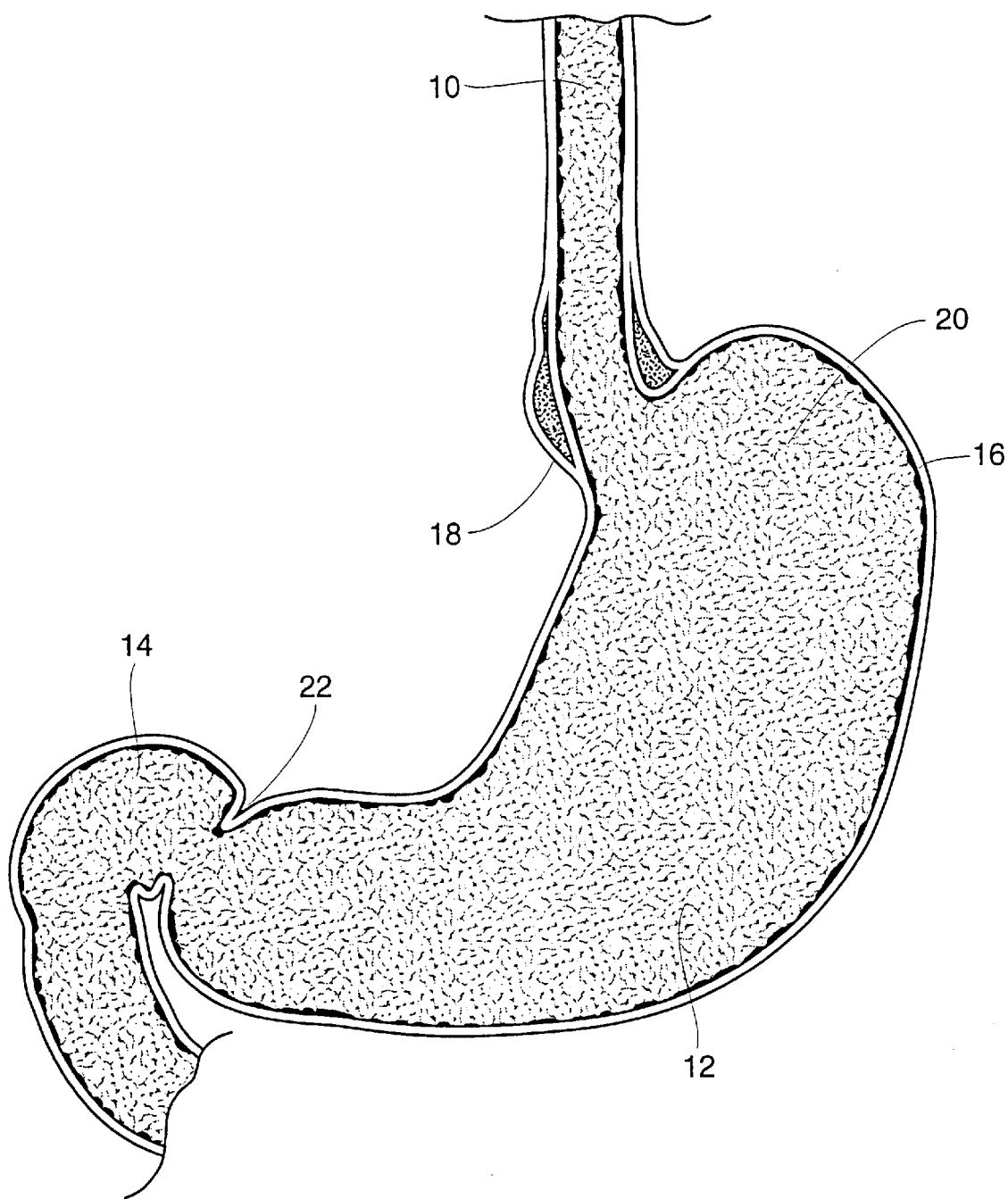

It should be noted that the views of the esophagus and stomach shown in the drawings are not intended to be strictly accurate in an anatomic sense. The drawings show the esophagus and stomach in somewhat illustrative form to demonstrate the features of the invention.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

Figure 2:
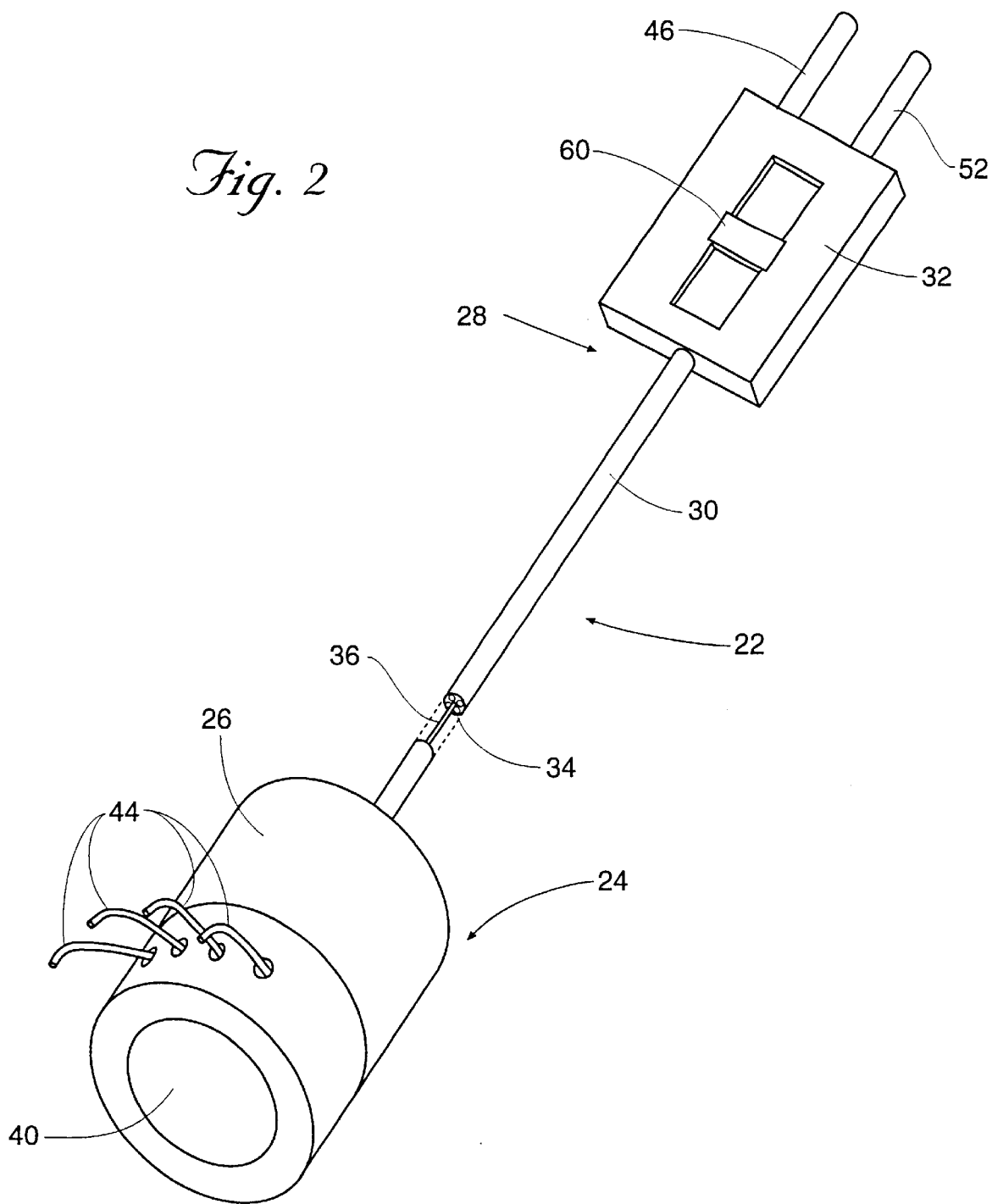

FIG. 2 shows a device 22 for deployment within the body for the purpose of treating a targeted tissue region. The device 22 is well suited for treating dysfunction of sphincters and adjoining tissue regions. In particular, the device can be used to treat dysfunctions in and around the upper gastrointestinal tract, e.g., the lower esophageal sphincter 18 and adjacent cardia 20 of the stomach 12, shown in FIG. 1. For this reason, the device and methods involving its use will be described in this context.

Still, it should be appreciated that the device 22 and associated methods are applicable for use in treating other dysfunctions throughout the gastrointestinal tract, e.g., the pharynx, esophagus, stomach, small intestine, colon, sigmoid, rectum, or anus as well as in other regions of the body, which are not necessarily sphincter-related. For example, the various aspects of the invention have application in procedures requiring treatment of hemorrhoids, or incontinence, or improving the barrier function or otherwise tightening interior tissue or muscle regions. Additionally, the device 22 can be used to ablate specific targets such as obstructions, nerve pathways, nerve ganglia, tumors, and other entities within the body.

As shown in FIG. 2, the device 22 includes an operative element 24. In the illustrated embodiment, the operative element 24 is carried within a body 26, made, e.g., of generally rigid medical grade plastic. Further details regarding the structure of the body 26 will be discussed later.

The operative element 24 can take different forms and can be used for either therapeutic purposes, or diagnostic purposes, or both. For example, the operative element 24 can include a mechanism to visualize body tissue, e.g., an ultrasonic transducer. The operative element 24 can also include a mechanism to deliver a drug or therapeutic material to body tissue. The operative element 24 can also include a mechanism for sensing a physiological characteristic in tissue, such as electrical activity, or for transmitting energy to stimulate or form lesions in tissue.

The operation of the operative element 24 is remotely controlled by a control assembly 28 appended to the body 26. The control assembly 28 includes a generally flexible, or at least generally non-rigid cable 30, made, e.g., from extruded plastic material. The operative element 24 is coupled to a distal end of the cable 30.

The proximal end of the cable 30 carries a control handle 32, which is sized to be hand-held and manipulated by a physician. As will be described later, the control handle 32 can contain various mechanisms, fluid connection sites, and electrical connection sites, which are linked through the cable 30 to the operative element 24. Through the handle 32, the physician remotely controls operation of the operative element 24.

The cable 30 can be constructed, for example, using standard flexible, medical grade plastic materials, like vinyl, nylon, poly(ethylene), ionomer, poly(urethane), poly (amide), and poly(ethylene terephthalate).

The cable 30 includes an array of interior lumens or channels 34, which carry various control wires, electrical wires, and fluid to and from the operative element 24. The lumens 34 may be integrally formed during extrusion of the cable 30. Alternatively, the lumens 34 can be formed by inserting a segmented support member 36 within the interior volume of cable 30. The presence of the support member 36 can provide additional internal support to increase the column strength of the cable 30.

In use, the operative element 24 is intended to be deployed into the body to a targeted tissue region. The cable 30 extends from the targeted tissue region to a location outside the body. There, the handle 32 is exposed for manual manipulation by a physician and for coupling to ancillary equipment, as will be explained later.

Figure 3:
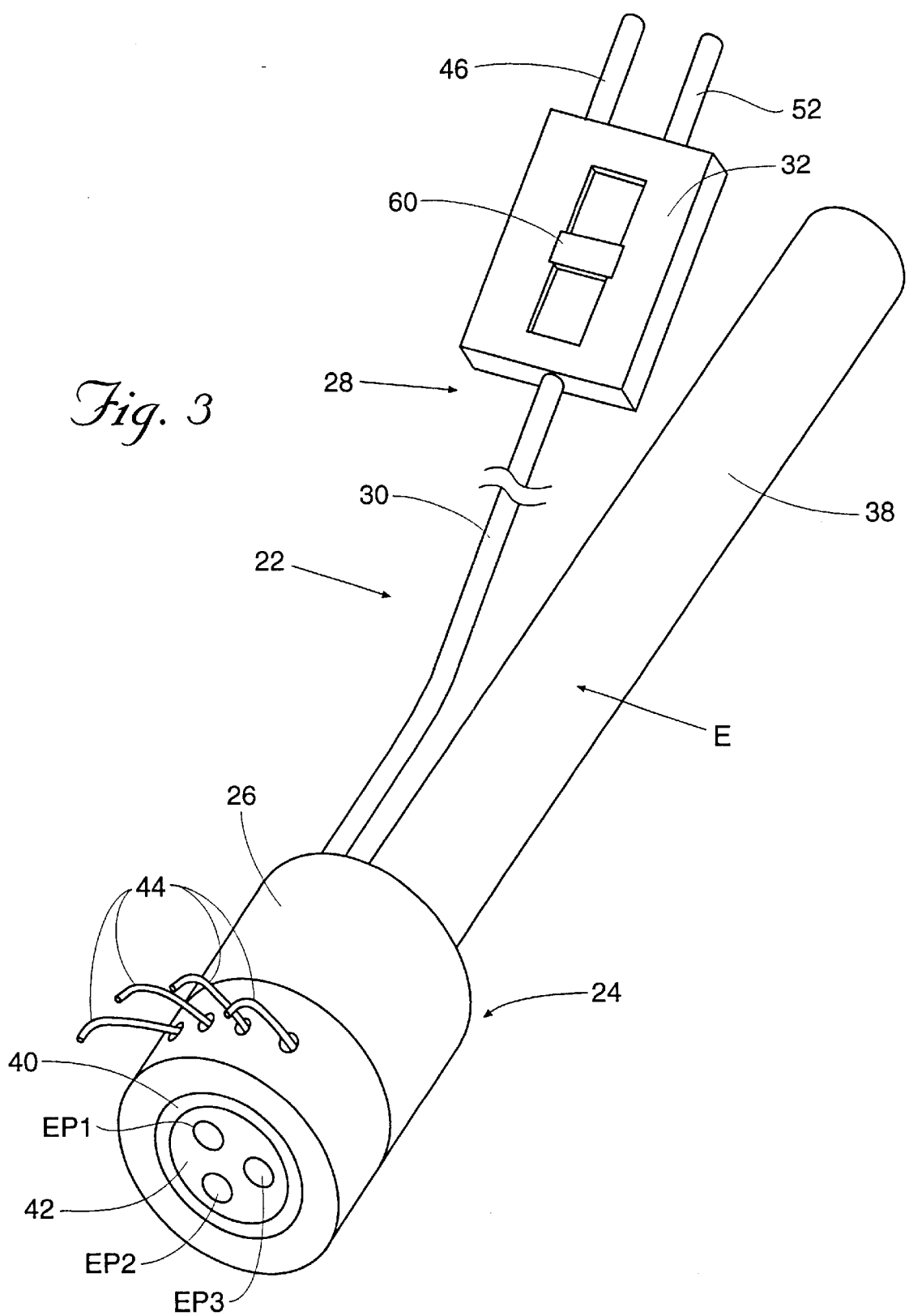

As FIG. 3 shows, the device is intended, during use, to be temporarily fitted to a separate catheter body 38. In the embodiment illustrated in FIGS. 2 and 3, the body 26 of the operative element 24 includes an interior cavity 40. As FIG. 3 shows, the cavity 40 is sized to allow the operative element body 26 to be removably fitted onto the distal end of the catheter body 38. In this arrangement, the catheter body 38 serves as the carrier for the operative element 24. In the capacity, the catheter body 38 serves to support and guide the operative element 24 during deployment and use in the targeted tissue region. The cable 30 can extend either along side the exterior of the catheter body 38 or through a lumen in the catheter body 38.

Figure 4:
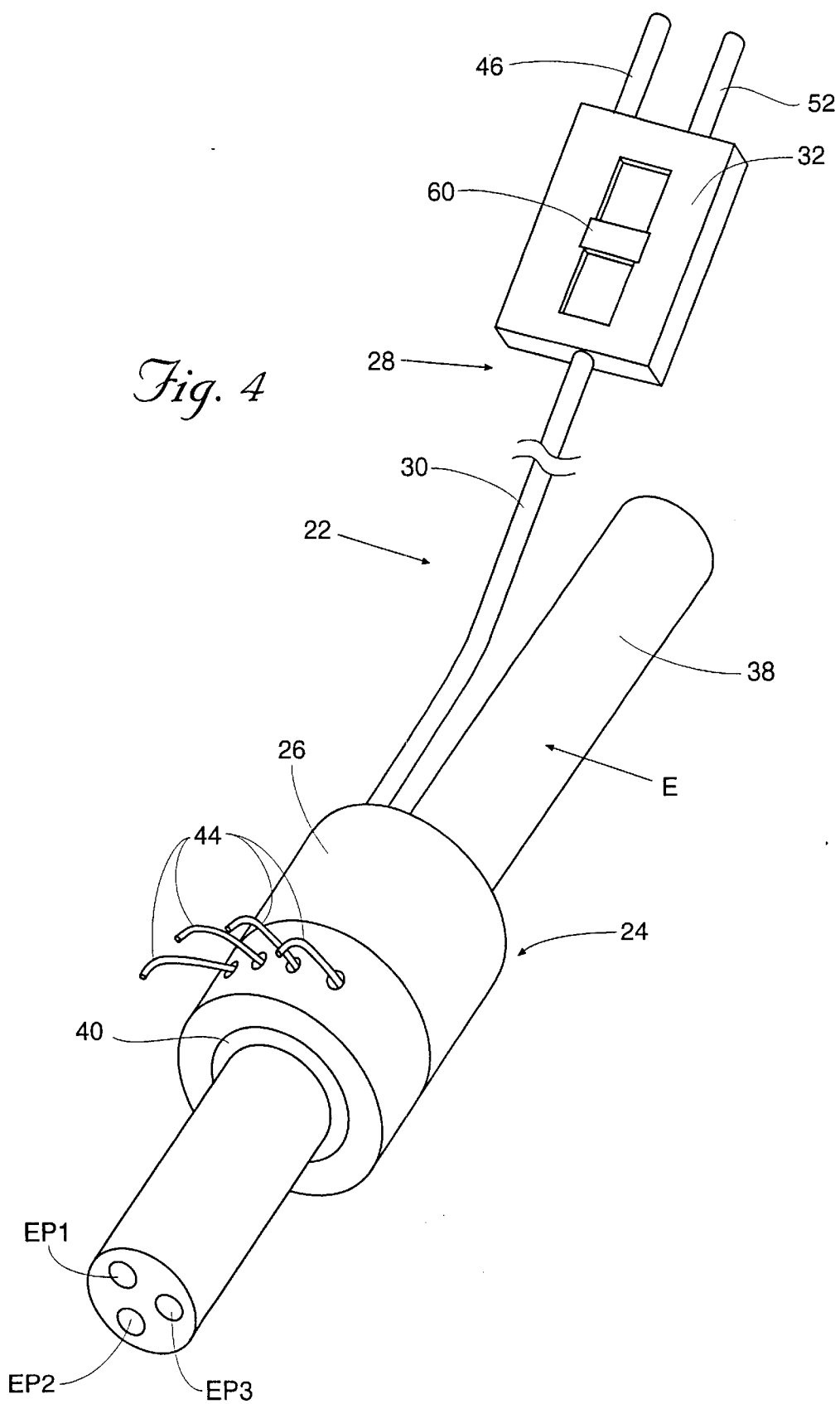

The cavity 40 can be configured either for releasable slidable engagement onto the distal end of the catheter body 38, as FIG. 3 shows. Alternatively, the cavity 40 can be configured for releasable snap-fit engagement about a side of the catheter body 38, as FIG. 4 shows. Snap-fit engagement can provide a smaller profile for the operative element 24, if so desired.

The releasable engagement of the operative element 24 on or about the catheter body 38 can be achieved is various ways, e.g., by a friction interference grip or mechanical fastening. Also, an ancillary flexible urethane or silicone sleeve or an elastomeric collar can be provided on the operative element 24 body to releasably hold the operative element 24 on the catheter body 38.

The catheter body 38 can be variously constructed and used in different ways. The catheter body 38 can, e.g., comprise a simple catheter tube, the sole function of which is to carry the operative element 24. The catheter body 38 can also be equipped to perform other functions, in addition to and independent of the function of the operative element 24. For example, the catheter body 38 can include a conventional steering mechanism, that allows the physician to deflect and point the catheter body 38 during its introduction into the targeted tissue region. The steering of the catheter body 38 can be used to guide and orient the operative element 24 carried by the catheter body 38.

In the illustrated embodiment, the catheter body 38 provides conventional endoscope functions, and can even comprise a standard endoscope E (as FIGS. 3 and 4 show), which is typically flexible and 8 mm to 12 mm in diameter. The endoscope E can be used in conventional ways without association with the operative element 24. However, when fitted with the operative element 24, the endoscope E serves the additional function as a carrier of the operative element 24. The visualization capabilities that endoscope provides further aid in the guiding and orientation of the operative element 24 carried by the endoscope. Furthermore, the endoscope E can include a conventional steering mechanism. The steering mechanism aids both in the visualization of the targeted tissue region, as well as in the placement of the operative element 24 carried by the endoscope E in association with the targeted tissue region.

The operative element 24 is structurally configured to preserve the other, independent functions of the catheter body 38. For example, as FIG. 3 shows, the cavity 40 can be opened at the distal end of the operative element body 26, to define an operating window 42. The window 42 allows other functions of the endoscope E to be performed when the operative element 24 is present. Alternatively, in the snap fit embodiment (shown in FIG. 4), the distal end of the endoscope E extends beyond the confines of the operative element body 26. The body 26 of the operative element 24 thereby preserves, e.g., the use of an endoscopic visualization port EP1, an endoscopic vacuum port EP2, and an endoscopic irrigation port EP3 at the distal end of the endoscope E. If fluid flow is not required through the endoscope E, the window 42 can be shielded with a transparent or non-opaque material, if desired.

In the illustrated embodiment (FIGS. 2, 3, and 4), the operative element 24 carries one or more electrodes 44. The electrodes 44 perform the function of applying energy in a selective fashion to the targeted tissue region. The applied energy creates one or more lesions, or a prescribed pattern of lesions, in the targeted tissue region. Depending upon the configuration of the electrodes 44, the lesions can be formed on the surface of targeted tissue region, or, alternatively, the lesions can be formed below the surface of the targeted tissue region. The electrodes 44 can have a curved or straight configuration. The electrodes 44 can be arranged in a variety of spaced apart patterns, e.g., in quadrants encompassing approximately 90 degrees, or 120 degrees, 180 degrees, or fully circumferential, and can be mutually spaced apart by, e.g., 90 degrees, or more or less. The electrodes 44 can comprise tissue pentration electrodes, extending outward, e.g., by 2 mm to 12 mm into tissue. The electrodes 44 can also comprise surface electrodes that do not penetrate tissue.

For the treatment of the lower esophageal sphincter and/or adjoining cardia, the electrodes 44 are configured to form subsurface lesions in a manner that preserves and protects the mucosal surface against thermal damage. It has been discovered that natural healing of the subsurface lesions leads to a physical tightening of the sphincter and/or adjoining cardia. The subsurface lesions can also result in the interruption of aberrant electrical pathways that may cause spontaneous sphincter relaxation. In any event, it has been discovered that the treatment can restore normal closure function to the sphincter.

In this arrangement (see FIG. 5), an electrical connector 46 on the handle 32 is linked by wires 48 extending through one of the lumens 34 in the cable 30 to the electrodes 44. An external generator 50 can be coupled to the connector 46. The generator 50 supplies treatment energy to the electrodes 44.

In a preferred embodiment, the generator 50 supplies radio frequency energy, e.g., having a frequency in the range of about 400 kHz to about 10 mHz. Of course, other forms of energy can be applied, e.g., coherent or incoherent light; heated or cooled fluid; resistive heating; microwave; ultrasound; a tissue ablation fluid; or cryogenic fluid.

In the illustrated embodiment, a luer fitting 52 on the handle 32 is linked by one of the lumens 34 in the cable 30 to the operative element 24. A fluid delivery apparatus 54 can be coupled to the fitting 52. As will be described later, the apparatus 54 supplies a fluid that is released by the operative element 24 to cool the targeted tissue region during application of the treatment energy.

A controller 56 includes a central processing unit (CPU). The controller 56 is linked to the generator 50 and the fluid delivery apparatus 54. The controller 56 governs the power levels, cycles, and duration that the radio frequency energy is distributed to the operative element 24, to achieve and maintain power levels appropriate to achieve the desired treatment objectives. In tandem, the controller 56 can also govern the delivery of cooling fluid.

The controller 56 can also include an input/output (I/O) device 58, allowing the physician to input control and processing variables, to enable the controller 56 to generate appropriate command signals. The I/O device 58 also receives real time processing feedback information from one or more sensors associated with the operative element 24 (as will be described later), for processing by the controller, e.g., to govern the application of energy and the delivery of processing fluid. The I/O device can also include a graphical user interface (GUI), to graphically present processing information to the physician for viewing or analysis.

Figure 6:
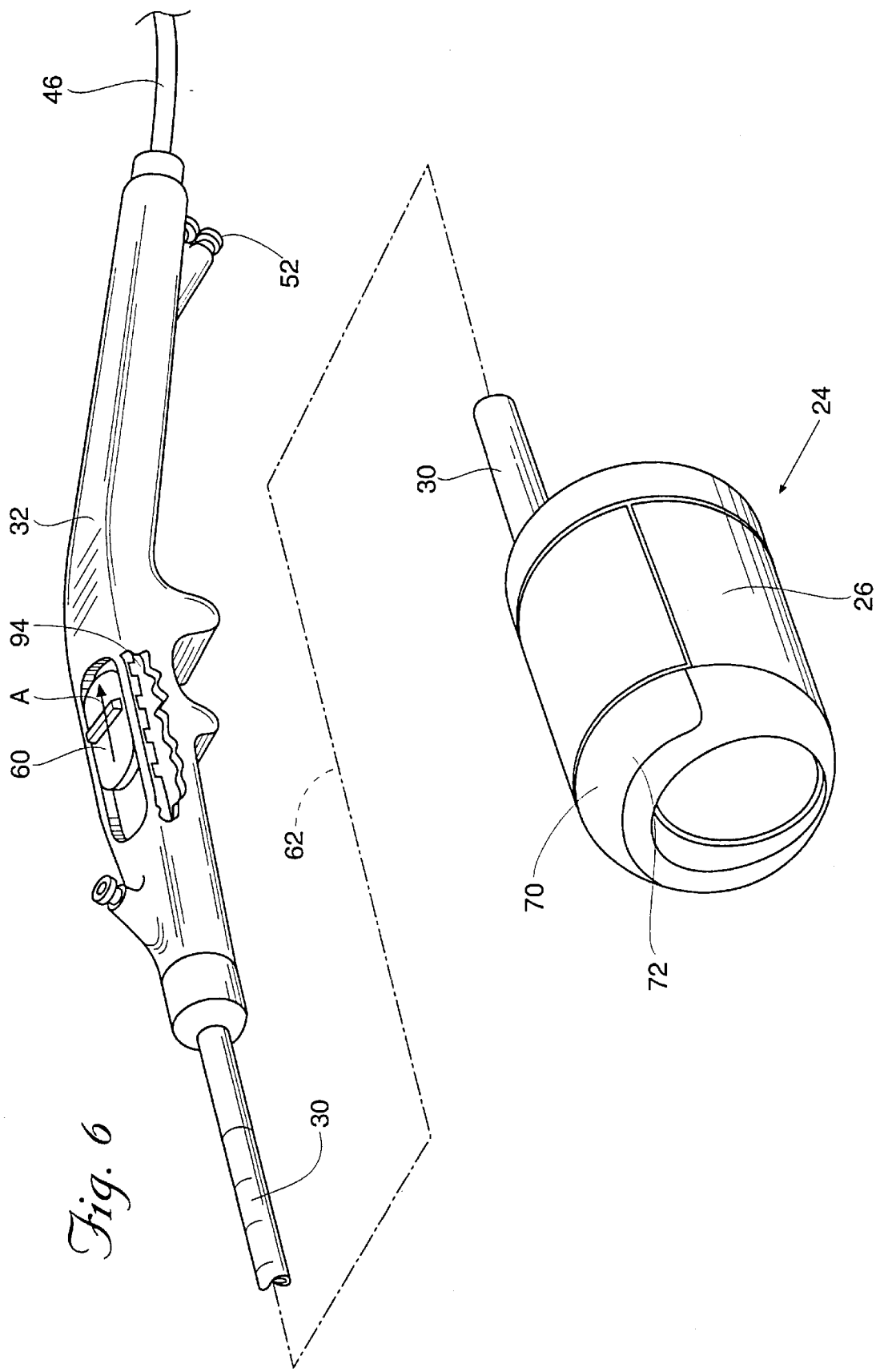
Figure 7:
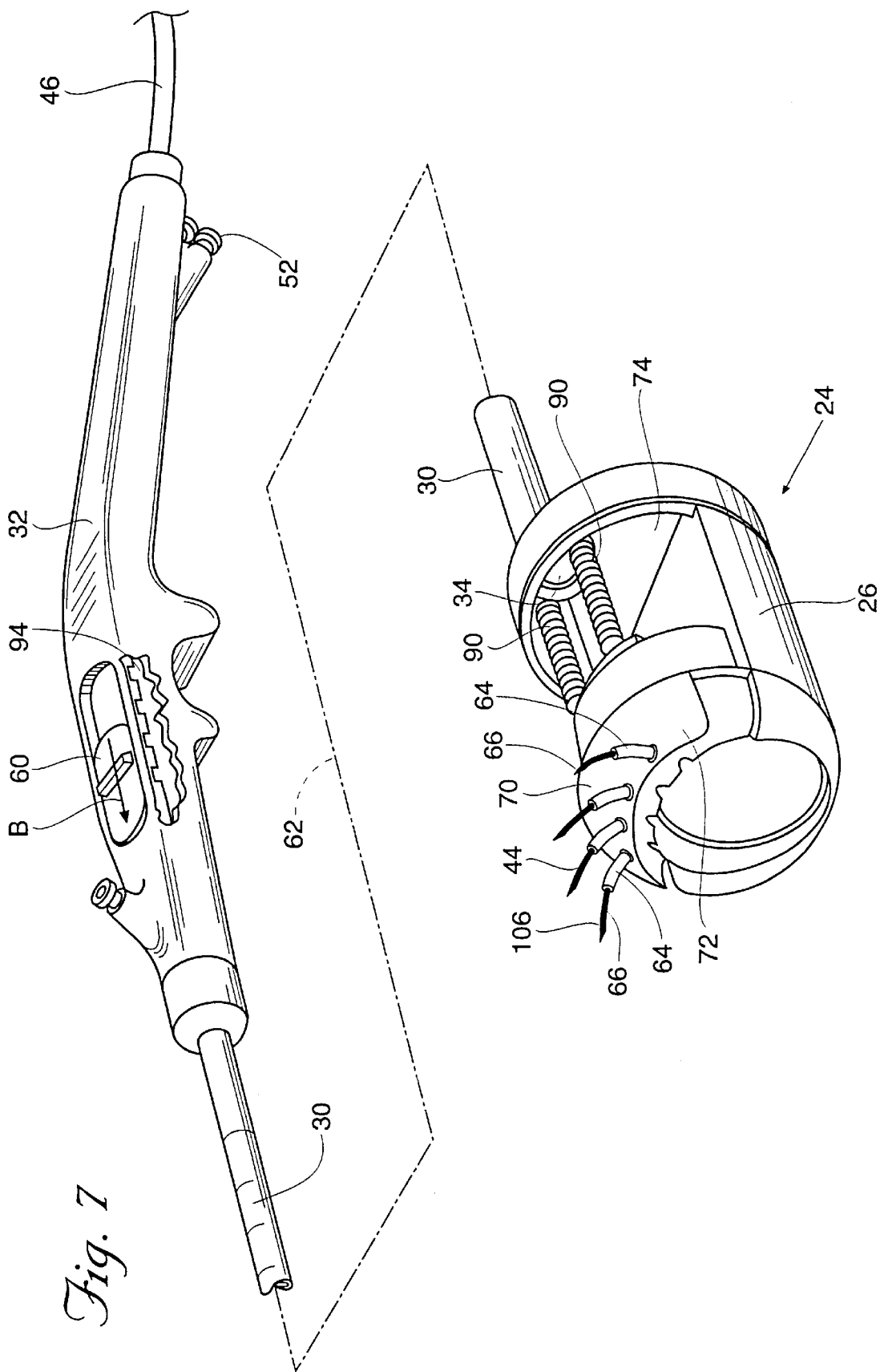

The embodiment of the operative element 24 shown in FIGS. 6 and 7 contemplates use of the operative element 24 to treat the lower esophageal sphincter and/or adjoining cardia. In this context, there are four electrodes 44 (shown in FIG. 7), which are arranged in a side-by-side, arcuate (i.e., curved) array on the distal end of the body 26. Of course, the number of electrodes 44 can vary, as can the geometric array of the electrodes 44.

As further shown in FIGS. 6 and 7, each electrode 44 moves with respect to the body 26 between a retracted position, withdrawn in the body 26 (see FIG. 6), and an extended position, extending outward from the body 26 (see FIG. 7).

A control mechanism 60 on the handle 32 is coupled to the movable electrodes 44 by at least one interior wire 62, which extends through lumens 34 in the cable 30. Manipulation of the control mechanism 60 (shown by arrows A and B in FIGS. 6 and 7) remotely moves the electrodes 44 in tandem between the retracted position and the extended position.

In use, the body 26 (fitted to the catheter body 38) is deployed and positioned with respect to the targeted tissue region, with the electrodes 44 retracted. The electrodes 44 can then be advanced. Further manipulation of the catheter body 38 moves the operative element body 26 into the desired association with the targeted tissue region. The electrodes 44, when advanced, penetrate surface tissue. In this way, the electrodes 44 can be caused to reach the lower esophageal sphincter or a submucosal layer of the cardia. The radio frequency treatment energy is transmitted by the electrodes 44 to surrounding tissue mass.

The surface of each electrode 44 can, e.g., be smooth, or textured, or concave, or convex.

The electrodes 44 can be formed in various sizes and shapes, such as a circular cross sectional shape. However, at least a portion of each electrode 44 preferably possesses a cross section that provides increased resistance to twisting or bending as the electrodes 44 penetrate tissue. For example, the electrodes 44 can possess a rectangular cross section, an elliptical cross section, pig tail, as well as conical or pyramidal, used to resist twisting.

To further facilitate penetration and anchoring in the esophagus or cardia, each electrode 44 is preferably biased with a bend. The electrodes 44 can be bent in either an antegrade direction (bending toward the proximal end of the body 26, as FIG. 7 shows) or in a retrograde direction (bending in the direction of the distal end of the body 26, as FIGS. 2 to 5 show) in an arc of ninety degrees or less.

The electrodes 44 can be formed from various energy transmitting materials. In the illustrated embodiment, for deployment in the esophagus or cardia, the electrodes 44 are formed from nickel titanium. The electrodes 44 can also be formed from stainless steel, e.g., 304 stainless steel. The electrodes 44 have sufficient distal sharpness and strength to penetrate a desired depth into the smooth muscle of the lower essophageal sphincter, or into the cardia wall. The desired depth can range from about 3 mm to about 8 mm for penetration into the esophageal or cardia wall. The selected length of the electrodes 44 will vary according to the anatomy of the targeted tissue region. For example, a tumor may require an electrode length as long as 2 cm.

A given electrode 44 can comprise a hybrid of materials, e.g., stainless steel for the proximal portion and nickel titanium alloy for the distal portion. The nickel titanium alloy performs best in a curved region of the electrode, due to its super-elastic properties. The use of stainless steel in the proximal portion can reduce cost, by minimizing the amount of nickel titanium alloy required.

The different materials may be joined, e.g., by crimping, swaging, soldering, welding, or adhesive bonding, which provide electrical continuity between or among the various materials. One or both of the materials may be flattened to an oval geometry and keyed together to prevent mutual twisting. In a preferred embodiment, the proximal portion comprises an oval stainless steel tube, into which a distal curved region having a round cross section and made of nickel titanium is slipped and keyed to prevent mutual twisting.

In the illustrated embodiment, an electrical insulating material 64 (see FIG. 7) is coated about the proximal end of each electrode 44. The electrical insulating material 64 insulates the mucosal surface of the esophagus or cardia from direct exposure to the radio frequency energy. Thermal damage to the mucosal surface is thereby avoided. As will be described later, the mucosal surface can also be actively cooled during application of radio frequency energy, to further protect the mucosal surface from thermal damage.

The electrical insulating material 64 can comprise, e.g., a Polyethylene Terephthalate (PET) material, or a polyimide or polyamide material. For deployment in the esophagus or cardia, the length of the material 64 ranges from about 8 mm to about 12 mm. For deployment in the esophagus or cardia, each electrode 44 preferably presents an exposed, non-insulated conductive length of about 8 mm, providing an exposed surface area at the distal end of each electrode 44 of preferably about 0.1 mm$^2$ to about 13 mm$^2$.

The surface area of the exposed region on the electrodes 44 affects the impedance of the electrodes 44 during use. Generally speaking, the larger the surface area of the exposed region is, the lower the expected impedance value is, leading to a fewer incidences of power shut-off due to high impedance.

Each electrode 44 can also carry a temperature sensor 66 (see FIG. 7), coupled to the input/output (I/O) device 58 and controller 56 via wires 68 that extend through lumens 34 in the cable 30. In the illustrated embodiment (see FIG. 7), each electrode 44 carries two temperature sensors 66, one at the base of the electrode 44, and the other at the tip of the electrode 44. Alternatively, the temperature sensor 66 at the base of the electrode can, instead, be carried by the body 26.

In use, the controller 56 samples the temperature sensed by the sensors 66. At the controller 56 and I/O device 58, an operator can select between several temperature control protocols, including average temperature control or hottest sensed temperature to serve as the input to control the magnitude of power to the electrodes 44. The electrodes 44 can be operated in either a monopolar mode or a bipolar mode.

The body 26 of the operative element 24 as above described can be variously constructed. For example, in the embodiment shown in FIGS. 6 and 7, the body 26 includes an electrode shield 70 that overlays the electrodes 44. In the embodiment shown in FIGS. 5 and 6, the electrode shield 70 comprises a region of penetrable material 72, through which the electrodes 44 can be advanced and retracted. The material 72 can include a closed cell structured material including semi-rigid foam insulation material, e.g., Styrofoam material, polyethylene or urethane foam, neoprene, cork, rubber, soft plastic, or any number of comparable materials.

The electrode-penetratable material 72 can also be selected to be permeable to or to retain the cooling fluid, e.g., an open cell material, such as open celled foam or another sponge-like, liquid retaining material. Cooling fluid can be conducted from the apparatus 54 through a lumen 34 in the cable 30 into an interior chamber 74 in the body 26. The cooling fluid in the chamber 74 permeates through the material 72 of the electrode shield 70 to contact tissue. Alternatively, separate ports for conducting cooling fluid can be provided in the body 26.

Figure 9:
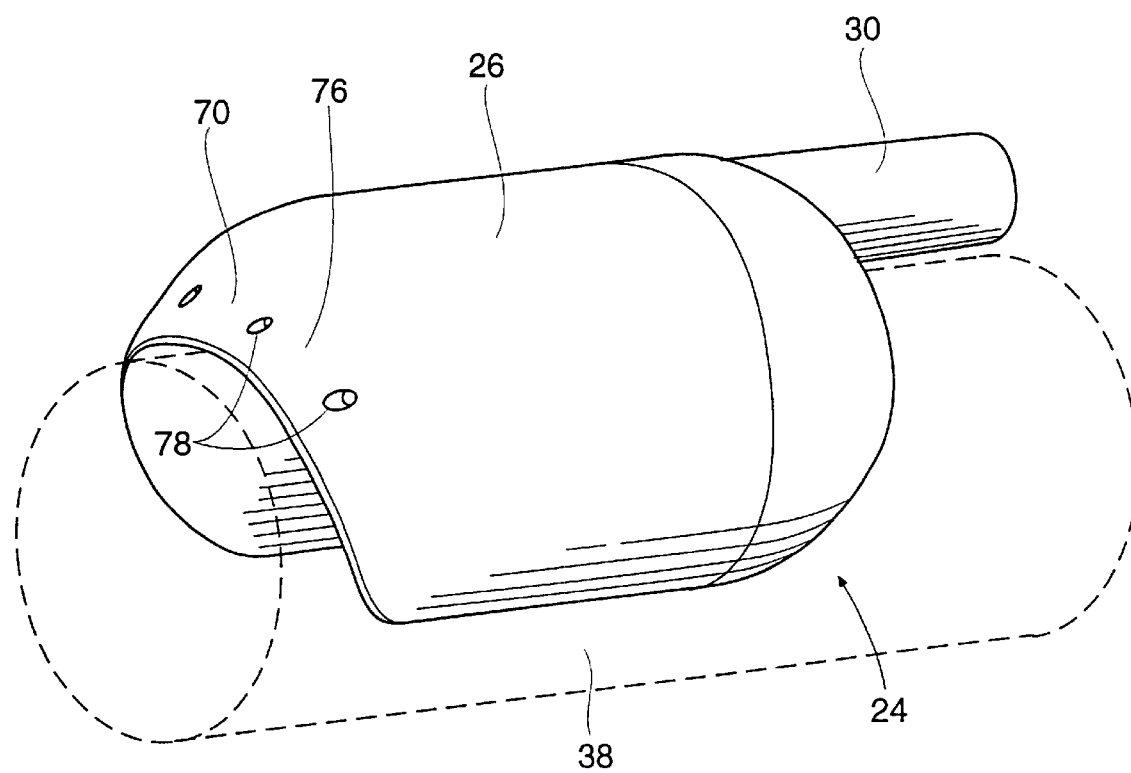

In an alternative embodiment (see FIG. 9), the electrode shield 70 comprises a region of rigid material 76 with formed openings 78, through which the electrodes 44 slide to advance or retract. The electrode openings 78 are of sufficient diameter to allow electrode passage, yet are sized small enough to avoid accumulating bodily debris, such as mucous. Cooling fluid can be dispensed from the chamber 74 through the electrode openings 78, as well. Alternatively, separate ports for conducting cooling fluid can be provided in the body 26. The body 26 shown in FIG. 9 is intended to engage the catheter body 38 (shown in phantom lines) in a snap-fit, as previously described.

In either arrangement, advancement of the electrodes 44 through the shield 70 can be accomplished in various ways, e.g., by spring action, a push-wire, a pull-wire, screw action, pneumatic means, or hydraulic means.

Figure 8:
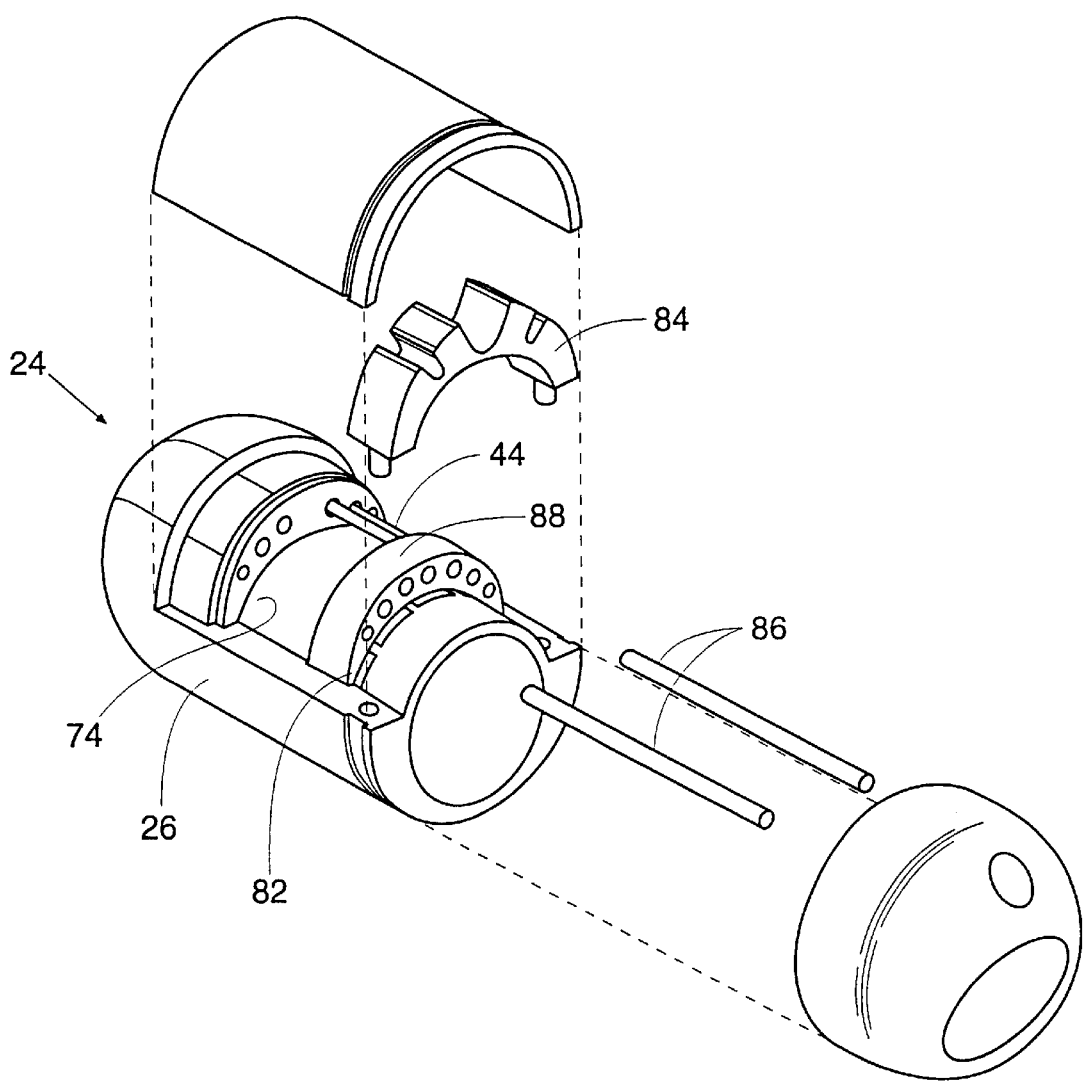

For example, as best shown in FIGS. 7 and 8, the electrodes 44 are joined to a carrier 88. The carrier 80 is joined to side tracks 82 in the chamber 74 by an overlaying bracket 84. The carrier 80 and bracket 84 slide as a unit forward and rearward, to advance and retract the electrodes 44.

Forward sliding movement of the carrier 80 advances the electrodes 44 through the shield 70 (as FIG. 7 shows). Rearward sliding movement of the carrier 80 retracts the electrodes 44 through the shield 70 (as FIG. 6 shows).

In this arrangement, the wire 62 that extends through a lumen 34 in the cable 30 can be attached, at one end, to the carrier 80 and, at the opposite end, to the control mechanism 60 on the handle 32. Pulling rearward on the control mechanism 60 (arrow A in FIG. 6) slides the carrier 80 rearward, away from the shield 70, to retract the electrodes 44 through the shield 70. Pushing forward on the control mechanism 60 (arrow B in FIG. 6) slides the carrier 80 forward, toward the shield 70, to advance the electrodes 44 through the shield 70. The push-pull wire 62 can be housed in a polyimide sleeve or stacked stainless steel coils for column strength.

In the embodiment shown in FIG. 7, springs 90 in the chamber 74 (which fit over the rails 86 shown in FIG. 8) normally bias the carrier 80 forward, toward the shield 70. In this arrangement, due to the springs 90, the electrodes 44 are normally biased toward an advanced position. In this arrangement, the wire 62 that extends through a lumen 34 in the cable 30 is attached, at one end, to the carrier 80 and, at the opposite end, to the control mechanism 60 on the handle 32. Pulling rearward on the control mechanism 60 slides the carrier 80 against the bias force of the springs 90 rearward, away from the shield 70. This pulling action on the carrier 80 retracts the electrodes 44 through the shield 70. A detent 94 on the handle 32 can be provided to releasably lock the control mechanism 60 in the pulled-back position (shown in FIG. 6), keeping the electrodes 44 retracted against the force of the springs 90. Releasing the mechanism 60 from the detent 94 causes the electrodes 44 to spring into the advanced position. Alternatively, the springs 90 in the chamber 74 could, instead, reside in the handle 32 and be coupled directly to the control mechanism 60.

Alternatively, springs 90 in the body chamber 74 or handle 32 could normally bias the sliding carrier 80 rearward, away from the shield 70. In this arrangement, due to the springs 90, the electrodes 44 are normally biased toward a retracted position. In this arrangement, the wire 62 extends through the cable 30 between the carrier 80 and control mechanism 60 on the handle 32. Pushing forward on the control mechanism 60 pushes the carrier 80 against the bias force of the springs 90 forward, toward the shield 70. This pushing action on the carrier 80 advances the electrodes 44 through the shield 70. The detent 94 can normally hold the control mechanism 60 in the pushed-forward position (shown in FIG. 7). Release of the control mechanism 60 from the detent 98 causes the electrodes 44 to spring into the retracted position.

Figure 10:
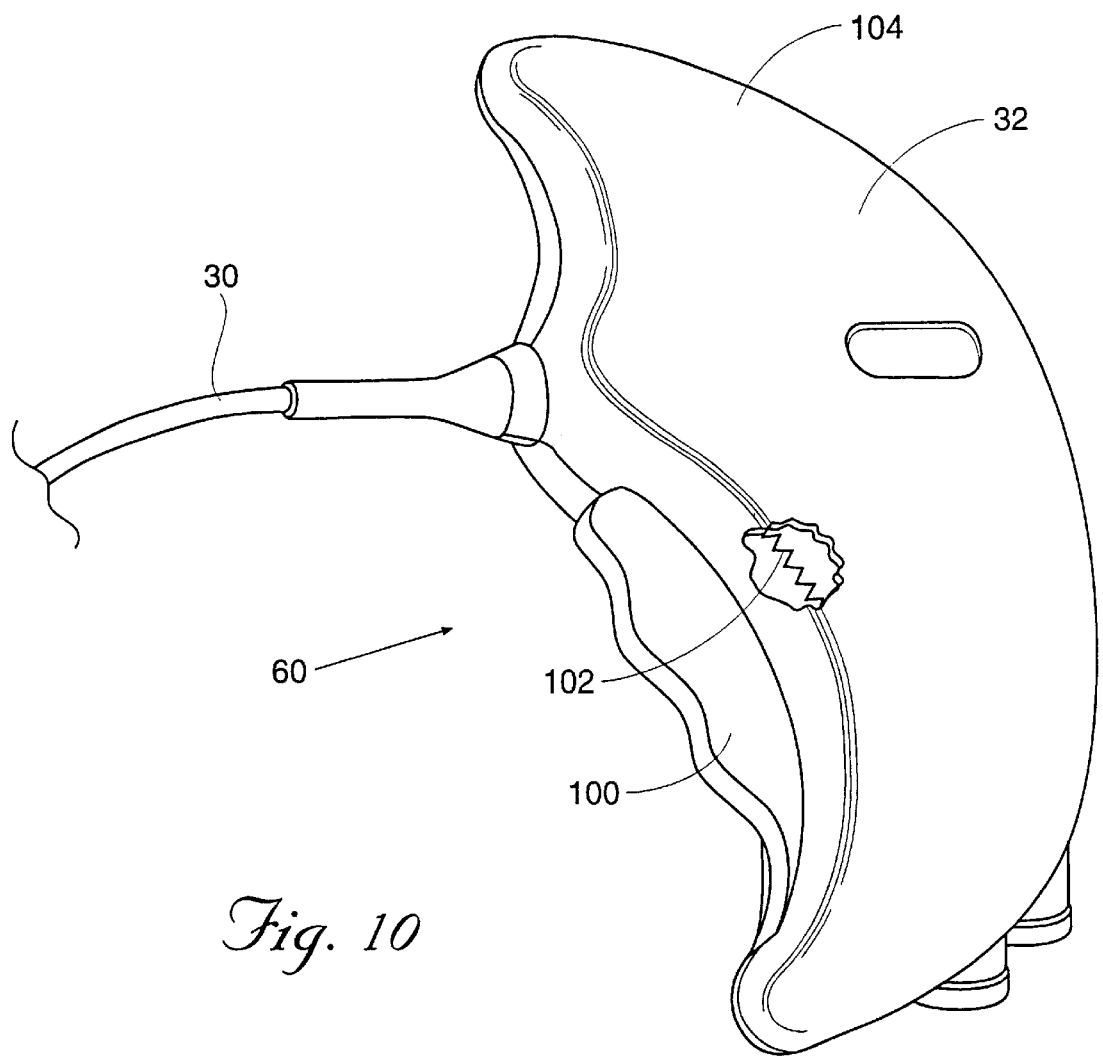
FIG. 10 is a perspective view of an alternative handle that can be used in association with an operative device like that shown in FIG. 6 or FIG. 9, showing a trigger-actuated mechanism for advancing the electrodes.

As shown in FIG. 10, the control mechanism 60 on the handle 32 can take the form of a trigger 100. When the electrodes 44 are spring biased toward the extended position, pulling the trigger 100 retracts the electrodes 44 through the shield 70. In this arrangement, the trigger 100 can include an internal ratchet mechanism 102, to provide a tactile indication of electrode retraction. For each click of the rachet mechanism 102, the physician knows that the electrodes 44 have been withdrawn a set distance, e.g., 1 mm. To disengage the ratchet mechanism 102, a ratchet disengagement button 104 can be disposed on the handle 32.

When the electrodes 44 are spring biased toward an retracted position, pulling the trigger 100 can advance the electrodes 44. In this arrangement, the ratchet mechanism 102 can be used to tactilely gauge the extent of electrode advancement.

When the control mechanism 60 requires the physician to apply manual force to advance the electrodes 44, each electrode 44 can carry a limit collar 106 (one of which is shown in FIG. 7 for the purpose of illustration). The limit collar 106 controls the depth of penetration. The limit collar 106 contacts surface tissue when a set maximum desired depth of electrode penetration has been reached. The contact between the collar 106 and surface tissue resists further advancement of the electrode 44. The physician senses the contact between the collar 106 and surface tissue by the increased resistance to electrode advancement, The physician thereby knows that the maximum desired depth of tissue penetration has been reached and to extend the electrodes 44 no further. A structure and function equivalent to the limit collar 106 can be created when different materials are used to form the electrode 44, as previously described. The cross-section of the proximal stainless steel portion can be sized greater than the cross section of the distal nickel-titanium portion. The difference in cross sections creates an enlarged transitional area that provides increased resistance to tissue penetration.

An electrical measurement can also be made to determine penetration of an electrode 44 in tissue. For example, by applying electrical energy at a frequency (e.g., 5 kHz) less than that applied for lesion formation, impedance of a given electrode 44 can be assessed. The magnitude of the impedance varies with the existence of tissue penetration and the depth of tissue penetration. A high impedance value indicates the lack of tissue penetration. The impedance value is lowered to the extent the electrode 44 penetrates the tissue.

The handle 32, cable 30, and operative element 24 can form an integrated construction intended for a single use and subsequent disposal as a unit. Alternatively, the handle 32 can comprise a nondisposable component intended for multiple uses. In this arrangement, the cable 30 and operative element 24 can comprise a disposable assembly, which the physician releasably connects to the handle 32 at time of use and disconnects and discards after use. The cable 30 can, for example, include a male plug connector that couples to a female plug receptacle on the handle 32.

Figure 11:
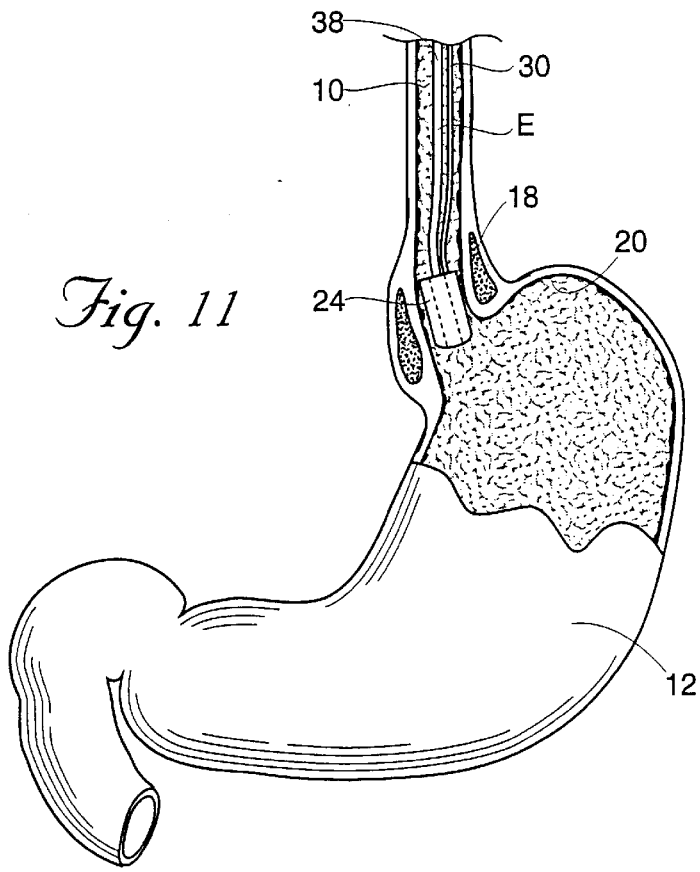
FIGS. 11 and 12 are side views of the esophagus and stomach, showing the antegrade deployment and use of a device like that shown in FIG. 2 to form lesions in the lower esophageal sphincter.

In use (see FIGS. 11 and 12), the physician deploys the operative element 24, fitted to the end of the catheter body 38, to the targeted tissue region, with the electrodes 44 in the retracted position. When the catheter body 38 or endoscope E includes a steering mechanism, the physician can orient the operative element 24 with the targeted tissue region by steering the catheter body 38. When the catheter body 38 comprises an endoscope E, the physician can also take advantage of the endoscopic visualization function to aid in the orientation of the operative element 24. Other visualization techniques, e.g., fluoroscopy or ultrasound, can be used as well.

Figure 13:
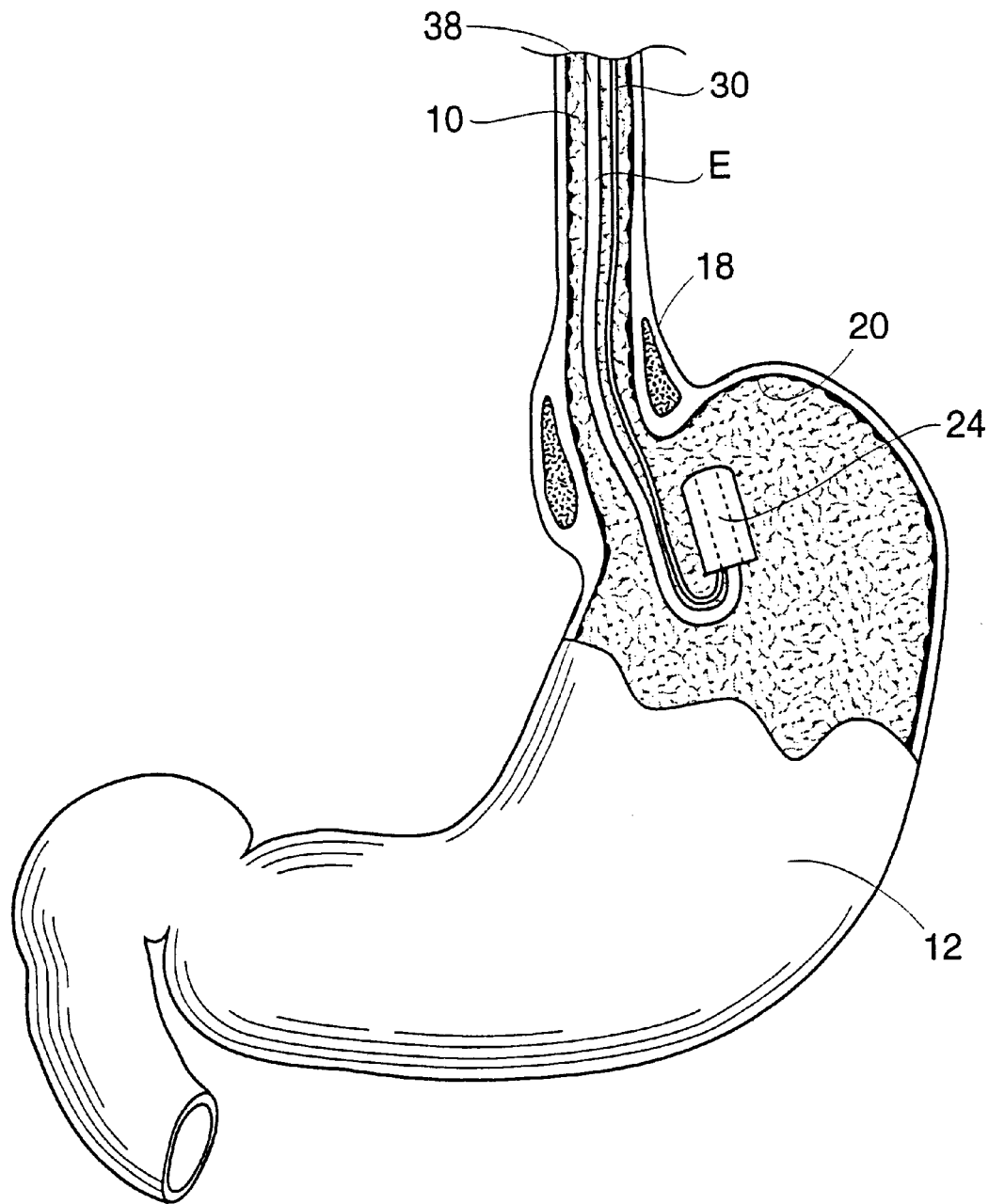
FIG. 13 is a side view of the esophagus and stomach, showing the retrograde deployment and use of a device like that shown in FIG. 2 to form lesions in the cardia.

The physician can deploy the operative element 24 antegrade to approach the lower esophageal sphincter and cardia. Alternatively (see FIG. 13), by flexing the catheter body or endoscope within the cardiac notch of the stomach, the operative element can be retroflexed to approach the cardia. The cable 30 can be configured to have a stiffer proximal end and a more flexible distal end to aid retroflexing.

Figure 12:
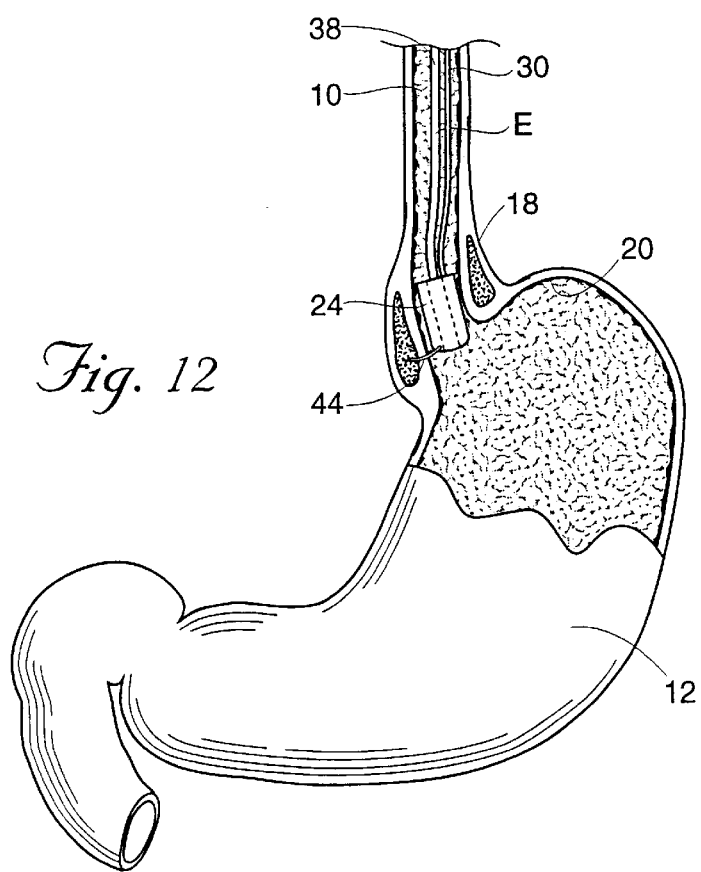

Once the operative element 24 is oriented in the desired way with the targeted tissue region, the physician advances the electrodes 44. With the electrodes 44 advanced outward, the physician can pull rearward on the catheter body 38 to move the advanced electrodes 44 into the tissue (as FIG. 12 shows). The physician applied energy through the electrodes 44, to ohmically heat tissue and form subsurface lesions.

Visual feedback can be provided to indicate to the physician that the electrodes 44 are deployed. For example, the body 26 can be made of a transparent material, to enable viewing from within the body 26, by deploying an endoscopic probe into the body 26 through a lumen in the cable 30. Alternatively, the body 26 can include a cantilevered indicator (not shown), which is deflected into the field of view of the carrier endoscope E when the electrodes 44 are advanced from within the body 26. The visual feedback serves as a reminder to the physician to retract the electrodes 44 before movement or withdrawal of body 26.

It is desirable to cool the mucosal surface while applying energy to ohmically heat tissue beneath a targeted treatment surface. The apparatus dispenses the cooling fluid through the cable 30 to be dispersed by the operative element 24.

In the embodiment shown in FIGS. 6 and 7, cooling liquid passes into the permeable material 72 of the shield 70. In this arrangement, the electrode shield 70 keeps the cooling fluid in contact with mucosal tissue at a localized position surrounding the electrodes 44.

Figure 5:
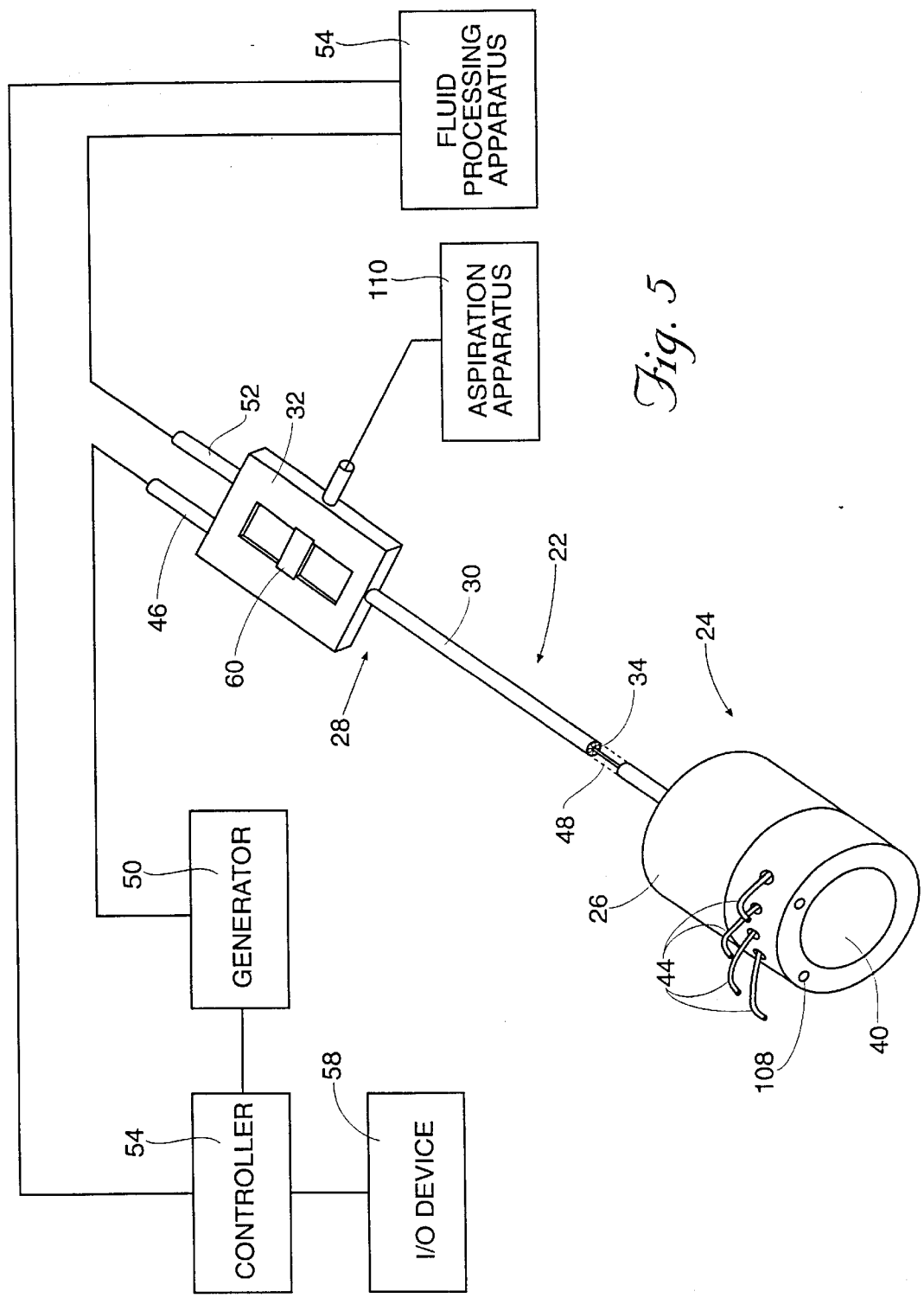

One or more ports 108 in the operative element 24 may be coupled by one or more interior lumens 34 in the cable 30 to an external fluid aspiration apparatus 110 (see FIG. 5). Alternatively, aspiration may be handled through the catheter body 38 or endoscope port EP2.

By absorbing and retaining the flow of cooling fluid, the material 72 of the electrode shield 70 minimizes aspiration requirements. The presence of the permeable material 72 in the electrode shield 70 also reduces the flow rate and volume of cooling fluid required to cool mucosal tissue, and could eliminate the need for aspiration altogether.

In the alternative embodiment shown in FIG. 8, the cooling fluid is dispensed through the electrode openings 78 or other ports provided. The cooling fluid residing in the chamber 74 can also be expelled in a bolus from the chamber 74 through the openings 78 by forward movement of the carrier 80, i.e., as the electrodes 44 are advanced. In this arrangement, the electrodes 44 can serve as valves, preventing flow through the openings 78 when retracted and permitting flow through the openings 78 when extended. The dispensed cooling fluid can be aspirated as previously described.

Upon formation of the lesions, the physician can move the catheter body 38 forward, to advance the electrodes 44 out of contact with the tissue. Alternatively, the physician can bring the electrodes 44 to the retracted position. By manually moving the catheter body 38, or by steering the distal end of the catheter body 38 to reposition the electrodes 44, or by rotating the catheter body 38, or by taking all three actions, the physician can reorient the electrodes 44 and cause the electrodes 44 to penetrate tissue in their reoriented position. In this way, the physician can, in succession, create a series of lesions to form a desired lesion pattern. It is desirable to create one or more symmetric rings of lesions with enough total volume to sufficiently shrink the lower esophageal sphincter or cardia.

Upon forming the desired lesion pattern, the physician advances the electrodes 44 out of contact with the tissue. The physician moves the electrodes 44 to the retracted position. In this condition, the physician can withdraw the catheter body 38 and operative element 24 from the targeted tissue region, thereby completing the procedure. At the completion of the procedure, the physician can remove the operative element 24 from the catheter body 38.

Various features of the invention are set forth in the following claims.

We claim:

1. An apparatus for treating a targeted tissue region in a body comprising a carrier including a cavity sized to allow the carrier to be temporarily mounted to an exterior of a catheter body for deployment on the catheter body into the targeted tissue region and to be removed from the catheter body following retrieval of the catheter body from the targeted tissue region, a tissue heating element on the carrier, and a control element coupled to the carrier to control operation of the tissue heating element while the carrier is fitted to the catheter body.

2. An apparatus according to claim 1 wherein the control element includes a cable having a distal end coupled to the carrier and a proximal end extending from the carrier and including a handle having a controller coupled through the cable to the tissue heating element.

3. An apparatus according to claim 1 wherein the tissue heating element includes at least one electrode for applying energy to the targeted tissue region.

4. An apparatus according to claim 3 wherein the control element includes a connector to couple the electrode to a source of electrical energy to apply electrical energy through the electrode to create a lesion in the tissue.

5. An apparatus according to claim 3 wherein the electrode is movable between a retracted position within the carrier and an extended position outside the carrier.

6. An apparatus according to claim 5 wherein the control element includes a controller that moves the electrode between the retracted and extended positions.

7. An apparatus according to claim 1 wherein the tissue heating element includes at least one electrode for applying radio frequency energy to the targeted tissue region.

8. An apparatus according to claim 5 wherein the control element includes a connector to couple the electrode to a source of radio frequency energy to apply electrical energy through the electrode to create a lesion in the tissue.

9. An apparatus according to claim 1 wherein the tissue heating element includes an array of electrodes for applying energy to the targeted tissue region.

10. An apparatus according to claim 9 wherein the control element includes a connector to couple the array of electrodes to a source of electrical energy to apply electrical energy through the electrodes to create a lesion pattern in the targeted tissue region.

11. An apparatus according to claim 9 wherein the electrodes in the array are movable between a retracted position within the carrier and an extended position outside the carrier.

12. An apparatus according to claim 11 wherein the control element includes a controller that jointly moves the electrodes between the retracted and extended positions.

13. An apparatus according to claim 1 wherein the tissue heating element includes an electrode having a non-cylindrical cross section.

14. An apparatus according to claim 13 wherein the non-cylindrical cross section is rectilinear.

15. An apparatus according to claim 13
wherein the non-cylindrical cross section is oval.
16. An apparatus according to claim 13
wherein the non-cylindrical cross section is elliptical.
17. An apparatus according to claim 1
wherein the tissue heating element includes an electrode having an axis, and
wherein the electrode is bent along the axis.
18. An apparatus according to claim 17
wherein the electrode is bent in an antegrade direction.
19. An apparatus according to claim 17
wherein the electrode is bent in a retrograde direction.
20. An apparatus according to claim 17
wherein the electrode is bent along the axis in an arc of less than ninety degrees.
21. An apparatus according to claim 17
wherein the electrode is bent along the axis in an arc of greater than ninety degrees.
22. An apparatus according to claim 1
wherein the tissue heating element includes an electrode carried by the carrier for advancement in a path to penetrate the tissue region, and
wherein the electrodes includes a tissue stop to resist tissue penetration beyond a selected depth.
23. An apparatus according to claim 1
wherein the tissue heating element includes an electrode having a proximal portion formed from a first material and a distal portion formed of a second material different than the first material.
24. An apparatus according to claim 23
wherein the electrode has an axis, and
wherein the distal portion is bent along the axis.
25. An apparatus according to claim 23
wherein the first material includes stainless steel and the second material includes nickel titanium.
26. An apparatus according to claim 1
further including a temperature sensor carried by the tissue heating element.
27. An apparatus according to claim 1
further including a temperature sensor carried by the carrier.
28. An apparatus according to claim 1
further including a dispensing element on the carrier to convey fluid to the targeted tissue region.
29. An apparatus according to claim 28
wherein the control element includes a connector to couple the carrier to a fluid source to convey fluid through the dispensing element to the targeted tissue region.
30. An apparatus according to claim 1
further including a aspirating element on the carrier to aspirate fluid from the targeted tissue region.
31. An apparatus according to claim 30
wherein the control element includes a connector to couple the carrier to a source of aspiration to convey fluid through the aspirating element from the targeted tissue region.
32. An apparatus according to claim 1
wherein the cavity is configured for releasable sliding engagement of the carrier upon the exterior of the catheter body.
33. An apparatus according to claim 1
wherein the cavity is configured for releasable snap-fit engagement of the carrier upon the exterior of the catheter body.
34. An apparatus according to claim 1
wherein the cavity is configured for releasable engagement of the carrier about an end of the catheter body.
35. An apparatus according to claim 1
wherein the cavity is configured for releaseable engagement about a side of the catheter body.
36. A system for treating a targeted tissue region in a body comprising
an endoscope comprising an endoscope body having an exterior, and a visualization element carried by the endoscope body,
a carrier including a cavity sized to allow the carrier to be temporarily fitted to the exterior of the endoscope body, without substantially interference with the visualization element, for deployment on the endoscope body into the targeted tissue region and to be removed from the endoscope body following retrieval of the endoscope body from the targeted tissue region,
a tissue heating element on the carrier, and
a control element coupled to the carrier to control operation of the tissue heating element while the carrier is fitted to the catheter body.
37. A system according to claim 36
wherein the cavity is configured for releasable sliding engagement of the carrier upon the exterior of the endoscope body.
38. A system according to claim 36
wherein the cavity is configured for releasable snap-fit engagement of the carrier upon the exterior of the endoscope body.
39. A system according to claim 36
wherein the cavity is configured for releaseable engagement of the carrier about an end of the endoscope body.
40. A system according to claim 36
wherein the cavity is configured for releaseable engagement about a side of the endoscope body.
41. A system according to claim 36
wherein the control element includes a cable having a distal end coupled to the carrier and a proximal end extending from the carrier and including a handle having a controller coupled through the cable to the tissue heating element.
42. A system according to claim 36
wherein the tissue heating element includes at least one electrode for applying energy to the targeted tissue region.
43. A system according to claim 42
wherein the control element includes a connector to couple the electrode to a source of electrical energy to apply electrical energy through the electrode to create a lesion in the tissue.
44. A system according to claim 42
wherein the electrode is movable between a retracted position within the carrier and an extended position outside the carrier.
45. A system according to claim 44
wherein the control element includes a controller that moves the electrode between the retracted and extended positions.
46. A system according to claim 36
wherein the tissue heating element includes at least one electrode for applying radio frequency energy to the targeted tissue region.

47. A system according to claim 46 wherein the control element includes a connector to couple the electrode to a source of radio frequency energy to apply electrical energy through the electrode to create a lesion in the tissue.

48. A system according to claim 36 wherein the tissue heating element includes an array of electrodes for applying energy to the targeted tissue region.

49. A system according to claim 48 wherein the control element includes a connector to couple the array of electrodes to a source of electrical energy to apply electrical energy through the electrodes to create a lesion pattern in the targeted tissue region.

50. A system according to claim 48 wherein the electrodes in the array are movable between a retracted position within the carrier and an extended position outside the carrier.

51. A system according to claim 50 wherein the control element includes a controller that jointly moves the electrodes between the retracted and extended positions.

52. A system according to claim 36 wherein the tissue heating element includes an electrode having a non-cylindrical cross section.

53. A system according to claim 36 wherein the tissue heating element includes an electrode having an axis, and wherein the electrode is bent along the axis.

54. A system according to claim 53 wherein the electrode is bent in an antegrade direction.

55. A system according to claim 53 wherein the electrode is bent in a retrograde direction.

56. A system according to claim 36 wherein the tissue heating element includes an electrode carried by the carrier for advancement in a path to penetrate the tissue region, and wherein the electrodes includes a tissue stop to resist tissue penetration beyond a selected depth.

57. A system according to claim 36 further including a temperature sensor carried by the tissue heating element.

58. A system according to claim 36 further including a temperature sensor carried by the carrier.

59. A system according to claim 36 further including a dispensing element on the carrier to convey fluid to the targeted tissue region.

60. A system according to claim 59 wherein the control element includes a connector to couple the carrier to a fluid source to convey fluid through the dispensing element to the targeted tissue region.

61. A system according to claim 36 further including a aspirating element on the carrier to aspirate fluid from the targeted tissue region.

62. A system according to claim 61 wherein the control element includes a connector to couple the carrier to a source of aspiration to convey fluid through the aspirating element from the targeted tissue region.

63. A system according to claim 36 wherein the endoscope includes a steering mechanism for deflecting the endoscope body.

* * * * *